(12) United States Patent
Nishioka et al.

(10) Patent No.: US 9,468,226 B2
(45) Date of Patent: Oct. 18, 2016

(54) FEED ADDITIVE, FEED, AND METHOD FOR PRODUCING FEED

(71) Applicants: Tohoku University, Sendai (JP); Mitsui Engineering & Shipbuilding Co., Ltd., Tokyo (JP)

(72) Inventors: Shunichiro Nishioka, Chiba (JP); Eri Ishikawa, Chiba (JP); Toshimi Tsukada, Chiba (JP); Masamori Kato, Tokyo (JP); Masaaki Toyomizu, Sendai (JP); Motoi Kikusato, Sendai (JP); Tomomi Kamizono, Sendai (JP)

(73) Assignees: Tohoku University, Sendai (JP); Mitsui Engineereing & Shipbuilding Co., Ltd., Tokyo (JP)

(*) Notice: Subject to any disclaimer, the term of this patent is extended or adjusted under 35 U.S.C. 154(b) by 0 days.

(21) Appl. No.: 14/237,505

(22) PCT Filed: Dec. 21, 2012

(86) PCT No.: PCT/JP2012/083235
§ 371 (c)(1),
(2) Date: Feb. 6, 2014

(87) PCT Pub. No.: WO2013/183189
PCT Pub. Date: Dec. 12, 2013

(65) Prior Publication Data
US 2015/0099710 A1    Apr. 9, 2015

(30) Foreign Application Priority Data
Jun. 8, 2012  (JP) ................................. 2012-121308

(51) Int. Cl.
| | |
|---|---|
| A23K 1/16 | (2006.01) |
| A61K 31/05 | (2006.01) |
| A61K 31/355 | (2006.01) |
| A61K 31/7004 | (2006.01) |
| C11C 5/00 | (2006.01) |

(52) U.S. Cl.
CPC ............ *A23K 1/1609* (2013.01); *A23K 20/10* (2016.05); *A23K 20/111* (2016.05); *A23K 20/163* (2016.05); *A23K 20/174* (2016.05); *A23K 50/75* (2016.05); *A61K 31/05* (2013.01); *A61K 31/355* (2013.01); *A61K 31/7004* (2013.01); *C11C 5/00* (2013.01)

(58) Field of Classification Search
USPC .................................................. 536/23, 128
See application file for complete search history.

(56) References Cited

U.S. PATENT DOCUMENTS

| | | | | |
|---|---|---|---|---|
| 4,206,245 A | * | 6/1980 | Drevici et al. ................ | 426/599 |
| 4,957,748 A | * | 9/1990 | Winowiski ........... | A23K 1/1631 |
| | | | | 426/2 |

FOREIGN PATENT DOCUMENTS

| | | |
|---|---|---|
| JP | 530922 | 2/1993 |
| JP | 9168367 | 6/1997 |
| JP | 2003088300 | 3/2003 |
| JP | 2006320206 | 11/2006 |
| JP | 2007267702 | 10/2007 |
| JP | 2011104517 | 6/2011 |

OTHER PUBLICATIONS

Hoong Chan Trading, EFB Fibre Has Turn Useless to Useful, http://article.hoongchan.com/efb-fibre-has-turn-yseless-to-useful.htm, 2009.*
Han, American Journal of Applied Sciences, 2012, 9 (11), 1862-1867, published online Sep. 5, 2012.*
Hasibuan, Asia-Pacific Jrnl of Chem. Eng, 2: 35-40, 2007.*
Tanaka ,(P 03219842, Sep. 1991, translation.*
Mandalari ,Journal of Food Composition and Analysis 23 (2010) 166-174.*
Tanaka ,(P 03219842, Sep. 1991, abstract.*
Rahman, Biochemical Engineering Journal 30 (2006) 97-103.*
Ibrahim, Materials Science and Engineering M108, Regional Symposium on Chemical Engineering 2005, Hanoi Horison Hotel, Hanoi, Vietnam, Nov. 30-Dec. 2, 2005.*
Driedger, Journal of Animal Science, vol. 34, No. 3, 1972.*
CBSNews, Deciphering Food Additives, Jun. 3, 2008, http://www.cbsnews.com/news/deciphering-food-additives/.*

* cited by examiner

*Primary Examiner* — Layla Berry
(74) *Attorney, Agent, or Firm* — K. David Crockett, Esq.; Niky Economy Syrengelas, Esq.; Crockett & Crockett, PC

(57) ABSTRACT

Objects are to provide an additive for a feed which can improve growth performance and meat quality of livestock, and can improve palatability of the feed, a feed and a method for preparing the feed, and the objects can be solved by an additive for a feed which comprises at least one or two or more of a polyphenol derived from EFB, α-tocopherol derived from EFB and xyloses derived from EFB, a feed which comprises an additive for a feed being added to a formulating material for a feed in the range of 0.05 to 20% by weight with a dry basis, and a method for preparing the feed.

1 Claim, 4 Drawing Sheets

FEED ADDITIVE, FEED, AND METHOD FOR PRODUCING FEED

TECHNICAL FIELD

The present invention relates to an additive for a feed, a feed and a method for preparing the feed, more specifically relates to an additive for a feed containing components derived from EFB, a feed and a method for preparing the feed.

BACKGROUND ART

In Shochu distillery by-product, which has been utilized as a livestock feed, amino acids such as glutaric acid, etc., and polyphenols, and crude protein components are also contained in addition to oxycarboxylic acids such as citric acid, etc., so that it has a high value as a starting material for a feedstuff.

Shochu distillery by-product contains a polyphenol in an amount of 1.5% by weight to 2.5% by weight or so, and it has a high value as a livestock feed, but a further value-added livestock feed has been demanded.

PRIOR ART DOCUMENTS

Patent Documents

Patent Document 1: JP 2007-267702A
Patent Document 2: JP 2011-104517A

SUMMARY OF THE INVENTION

Problems to be Solved by the Invention

Oil palm has been cultivated mainly in Malaysia, Indonesia, Thailand, Columbia, Nigeria, etc., and palm oil has been squeezed from the fruit of the oil palm. An empty fruit bunch after collecting the palm oil is called as EFB (Empty Fruits Bunch).

The present inventors have investigated whether an EFB extract can be utilized as an additive for a feed or not, and as a result, they have found out that it has excellent physical properties including a polyphenol content that is extremely high as compared with that of Shochu distillery by-product. When it is fed to livestock, it turned out that it improves growth performance and meat quality of the livestock, and further palatability of a feed can be improved.

Thus, an object of the present invention is to provide an additive for a feed which can improve growth performance and meat quality of the livestock, and improve palatability of the feed, and also to provide a feed and a method for preparing the feed.

Also, other objects of the present invention will be clarified by the following descriptions.

Means to Solve the Problems

The above-mentioned problems have been solved by the following respective inventions.

1. An additive for a feed which comprises at least one or two or more of a polyphenol derived from EFB, α-tocopherol derived from EFB and xyloses derived from EFB.

2. The additive for a feed according to 1, wherein it contains at least three kinds of a polyphenol derived from EFB, α-tocopherol derived from EFB and xyloses derived from EFB.

3. A feed which comprises the additive for a feed according to 1 or 2 being added to a formulating material for a feed in a range of 0.05 to 20% by weight with a dry basis.

4. A method for preparing a feed which comprises adding the additive for a feed according to 1 or 2 to a formulating material for a feed in a range of 0.05 to 20% by weight with a dry basis.

Effects of the Invention

According to the present invention, it can be provided an additive for a feed which can improve growth performance and meat quality of the livestock, and further improve palatability of a feed, a feed and a method for preparing the feed.

EMBODIMENTS TO CARRY OUT THE INVENTION

Figure 1:
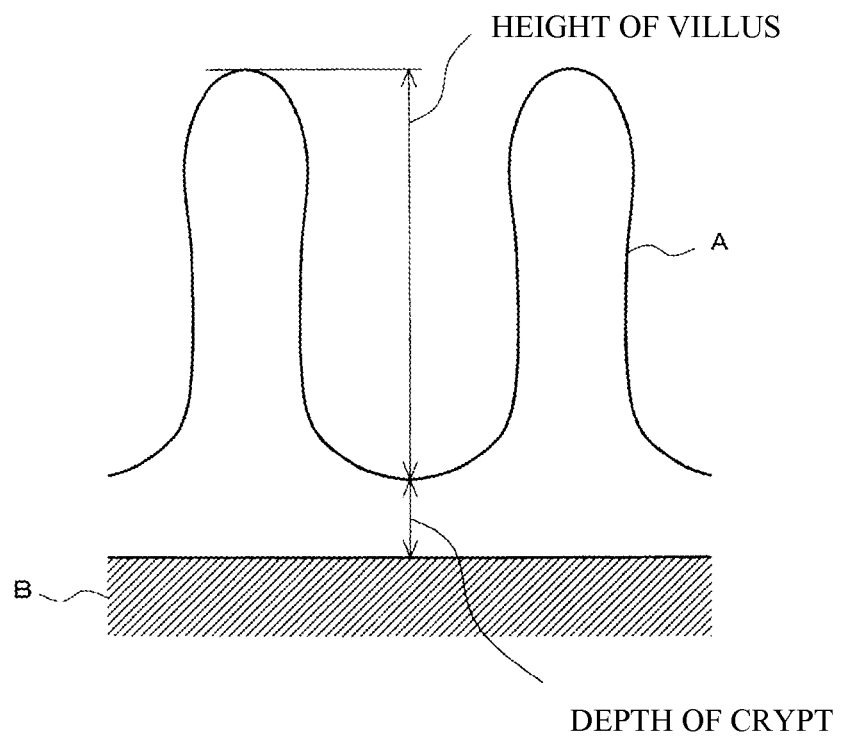
FIG. 1 Example; this is a drawing showing a measurement example of a height of villus and a depth of crypt at small intestine.

In the following, embodiments to carry out the present invention are explained.

<Additive for feed> The additive for a feed according to the present invention contains at least one or two or more of a polyphenol derived from EFB, an α-tocopherol derived from EFB and xyloses derived from EFB.

The polyphenol derived from EFB, the α-tocopherol derived from EFB and the xyloses derived from EFB contained in the additive for a feed according to the present invention are materials contained in the EFB extract extracted from the EFB, and the EFB extract can be obtained, for example, by subjecting the EFB to the hydrothermal treatment.

In the present invention, the terms "derived from EFB" mean that the EFB extract itself as such, or after suitable treatment, it is used as an additive for a feed according to the present invention.

The additive for a feed according to the present invention may be any form either of a liquid state or a solid state.

In the present invention, the polyphenol derived from EFB generically refers to a compound having a plural number of phenolic hydroxyl groups in one molecule contained in the EFB extract which is an additive for a feed according to the present invention, and specific examples thereof may be exemplified by flavonoids such as catechins, anthocyanin, flavone, isoflavone, fravan, flavanone, etc., phenols such as chlorogenic acid, etc., and those which are generally classified into polyphenols such as ellagic acid, lignan, curcumin, coumarin, etc.

The additive for a feed according to the present invention preferably contains 1 to 15% by weight of a polyphenol with a dry basis. "% by weight" with a dry basis means % by weight based on a material in which water is removed from the additive for a feed (herein after the same).

In the present invention, the content of the above-mentioned polyphenol is a value in which a 80% ethanol solution is added to the additive for a feed, the mixture is heated by hot bath at 80° C. for 30 minutes, then, subjected to centrifugation at 1600×g for 10 minutes, and the obtained supernatant is used as a sample solution and measured by the Folin-Denis method to obtain the content corresponding to a gallic acid.

In the present invention, the α-tocopherol derived from EFB means α-tocopherol contained in the EFB extract which is the additive for a feed according to the present invention, and the specific examples thereof may be exemplified by DL-α-tocopherol, DL-α-tocopherol acetate, DL-α-tocopherol succinate, etc.

The additive for a feed according to the present invention preferably contains 1 to 8 mg/100 g of α-tocopherol with a dry basis. "mg/100 g" with a dry basis means weight based on a material in which water is removed from the additive for a feed.

In the present invention, the content of the above-mentioned α-tocopherol is a value measured by the HPLC method.

In the present invention, the xyloses derived from EFB means xylose or a compound containing xylose as a partial structure contained in the EFB extract which is the additive for a feed according to the present invention. The compound containing xylose as a partial structure may be exemplified by an oligomer and a polymer of xylose, etc.

The additive for a feed according to the present invention preferably contains 1 to 15% by weight of xyloses with a dry basis.

In the present invention, the content of the xyloses is a value obtained by stirring the additive for a feed under 72% to 45% sulfuric acid at room temperature for 1 hour, diluting the sulfuric acid concentration to 2%, subjecting to an autoclave treatment at 121° C. for 1 hour, and an amount of the xylose in the resulting liquid is determined by the high performance liquid chromatography method (HPLC method). That is, it is a value of the xylose contained in the additive for a feed as well as the xylose formed by decomposition of the compound containing xylose as a partial structure.

According to the additive for a feed in accordance with the present invention, by containing at least one or two or more of the polyphenol derived from EFB, the α-tocopherol derived from EFB and the xyloses derived from EFB, growth of villus in the intestine is promoted whereby growth of the livestock can be expedited, further formation of a peroxide in a body is controlled to improve the property of the livestock meat, moreover, the effect of improving palatability of the feed can be obtained, mainly by the antioxidative effect of the components derived from EFB.

Also, the additive for a feed according to the present invention preferably contains at least two kinds of the polyphenol derived from EFB and the xyloses derived from EFB, at least two kinds of the polyphenol derived from EFB and the α-tocopherol derived from EFB, or at least two kinds of the xyloses derived from EFB and the α-tocopherol derived from EFB. According to this constitution, each of the components derived from EFB synergistically acts with each other, whereby it makes the effects of the present invention remarkable.

Further, when the additive for a feed according to the present invention contains three kinds of the polyphenol derived from EFB, the α-tocopherol derived from EFB and the xyloses derived from EFB, each of the components derived from EFB synergistically acts with each other, whereby it makes the effects of the present invention particularly remarkable.

<feed and preparation method thereof> The feed according to the present invention can be obtained by mixing the above-mentioned additive for a feed with a formulating material for a feed.

When the additive for a feed is a liquid state, for mixing the additive for a feed with a formulating material for a feed, these materials may be mixed by stirring in a mixing apparatus using a mixer, or may be employed a method such as coating and spreading, etc.

When the additive for a feed is a solid state, these materials may be mixed by stirring in a mixing apparatus using a mixer.

In the present invention, a mixture in which the additive for a feed is mixed with the formulating material for a feed may be subjected to compression molding to prepare pellets.

The formulating material for the feed which is an object to be added to the additive for a feed of the present invention is not particularly limited, and may comprise a single taste feed, a formulated feed, a mixed feed, a crude feed, a condensed feed and a chemical feed, etc.

Further, the formulating material for the feed may preferably contain a specific feed such as a salt, a calcium preparation, a shell, a vitamin compound, an amino acid, etc.

In addition, the additive for a feed according to the present invention is not limited only to a feed for the livestock such as a chicken, cattle, a pig, etc., but it is also preferred to use the same by adding to a feed for an animal other than the livestock such as a pet food, etc. It is also preferred to use the same by adding to a feed for fish breeding (fish food).

An amount of the additive for a feed to be added is preferably in the range of 0.05 to 20% by weight with a dry basis, more preferably in the range of 0.15 to 10% by weight with a dry basis, and most preferably in the range of 0.25 to 5% by weight with a dry basis based on the amount of the formulating material for the feed.

EXAMPLES

In the following, Examples of the present invention are explained. The present invention is not limited by these Examples.

1. Component Determination Test

Examples 1 to 3

EFB was subjected to the hydrothermal treatment to obtain a liquid state additive for a feed. According to the same manner as mentioned above, further additional two additives for a feed were obtained every other month. The obtained three additives for a feed were made Examples 1 to 3, respectively.

<Quantitative method> With regard to the obtained additives for a feed, quantitative analyses of moisture, polyphenol, α-tocopherol and xyloses were carried out according to the method mentioned below.

(i) Moisture

Quantitative analysis of the moisture was carried out by the normal pressure ustulation method.

(ii) Polyphenol

Quantitative analysis of the polyphenol was carried out by adding 80% ethanol solution to the additive for a feed, heating the mixture by hot bath at 80° C. for 30 minutes, then, centrifuged at 1600×g for 10 minutes, and making the obtained supernatant a sample solution and measuring the same by the Folin-Denis method to obtain the content corresponding to a gallic acid.

(iii) α-Tocopherol

Quantitative analysis of the α-tocopherol was carried out by the HPLC method.

The results of the quantitative analyses are shown in Table 1.

(iv) Xyloses

Quantitative analysis of the xyloses was carried out by subjecting the additive for a feed to the sulfuric acid-decomposition treatment and then by the HPLC method.

Comparative Example 1

As an additive for a feed for comparison, refined molasses (available from Shouyuu Kougyou Co., Ltd.) was determined in the same manner as in Example 1. The results of the quantitative analyses are shown in Table 1.

Comparative Examples 2 to 4

As additives for a feed for comparison, three kinds of concentrates of the supernatant of Shochu distillery by-product were determined in the same manner as in Example 1. The results of the quantitative analyses are shown in Table 1.

TABLE 1

|  | Ex. 1 | Ex. 2 | Ex. 3 | Comp. Example 1 | Comp. Example 2 | Comp. Example 3 | Comp. Example 4 |
|---|---|---|---|---|---|---|---|
| Origin | EFB | EFB | EFB | Refined molasses | Shochu dist. by-product | Shochu dist. by-product | Shochu dist. by-product |
| Polyphenol (% by weight) | 8.10 | 7.01 | 8.19 | — | 2.51 | 1.66 | 1.85 |
| α-Tocopherol (mg/100 g) | 2.6 | 2 | 5.78 | ND (<0.4) | 9.8 | — | — |
| Xyloses (% by weight) | 11.67 | 9.6 | 12.45 | ND (<0.2) | — | — | — |

*% by weight is a dry basis.

<Evaluation of Component Determination Test>

Additives for a feed of Examples 1 to 3 contain a polyphenol derived from EFB, α-tocopherol and xyloses, in particular, it can be understood that the polyphenol content is remarkably high.

2. Feeding Test

Example 4

The additive for a feed obtained in Example 1 was mixed with a formulating material for the feed in an amount of 1.00% by weight (0.54% by weight with a dry basis), attached and impregnated to prepare a feed, and fed. The composition, metabolic energy, gross energy and crude protein of the feed were shown in Table 2.

Object to be fed: 16 days-old Chunky broiler (female)
Term of feeding: 12 days up to 28 days-old (made free drinking and ceaseless feeding)
Number of broilers to be tested: 7 to 8 broilers <Observation of Shape of Small Intestine>

At 28 days-old, tissue preparation with a piece of 1 cm was collected from the duodenum, and 3 to 4 μm of segments were further cut therefrom and stained by the hematoxylin-eosin method.

10 sets of villus and crypt were randomly selected from the samples of two segments per a broiler, a height of villus and a depth of crypt were measured by using a microscope, and further a ratio of the height of villus to the depth of crypt was calculated from the measured values.

Incidentally, FIG. 1 is a drawing showing a measured example of the height of villus and the depth of crypt, and A shows villus and B shows a muscle layer.

Figure 2:
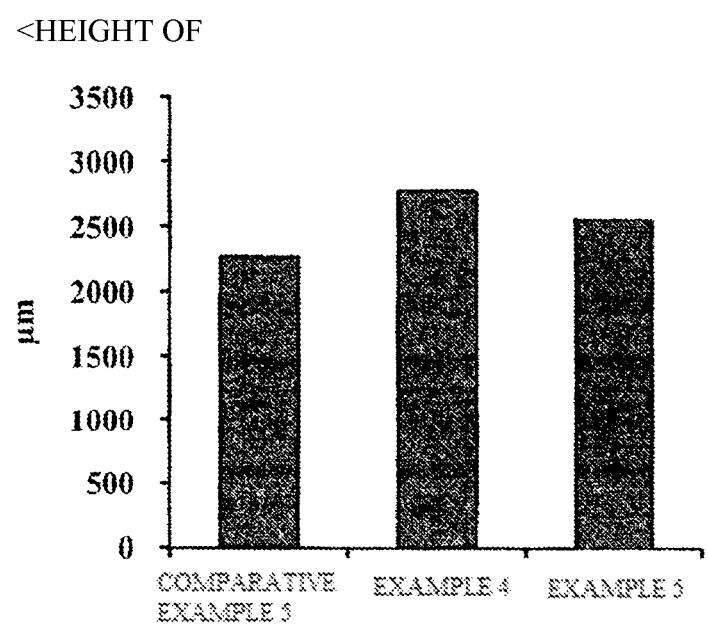
FIG. 2 Example; this is a drawing comparing a height of villus.
Figure 3:
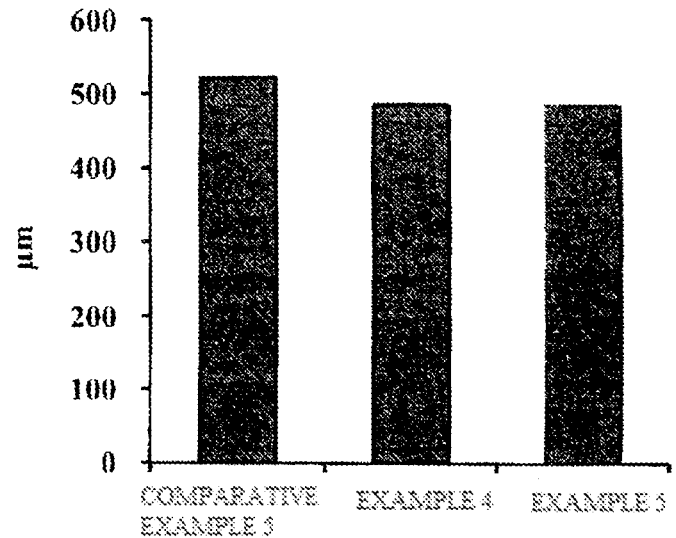
FIG. 3 Example; this is a drawing comparing a depth of crypt.
Figure 4:
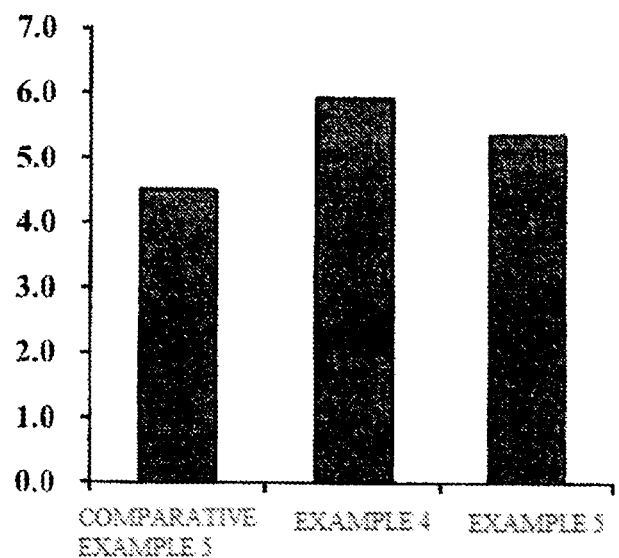
FIG. 4 Example; this is a drawing comparing a ratio of the height of villus to the depth of crypt.

The height of villus is shown in FIG. 2, the depth of crypt is shown in FIG. 3, and the ratio of the height of villus to the depth of crypt is shown in FIG. 4, respectively.

<Determination of Peroxide in Pectoralis Major Muscle>

Figure 5:
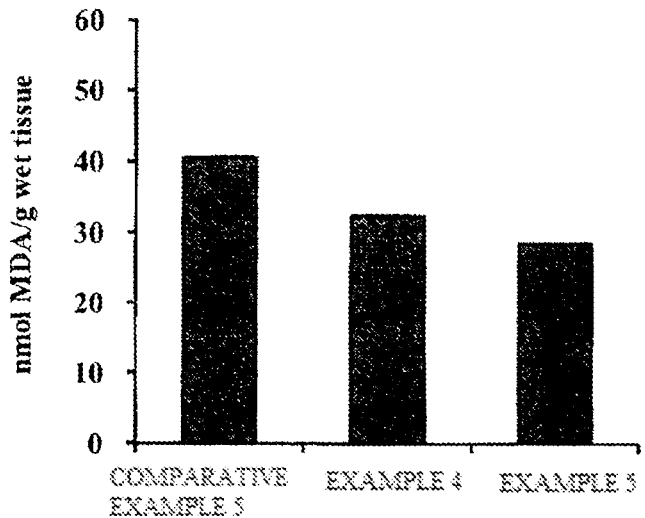
FIG. 5 Example; this is a drawing comparing a lipid peroxide amount of pectoralis major muscle.

A pectoralis major muscle tissue at 28 days-old was collected, and a lipid peroxide amount was determined by the colorimetric analysis (spectrophotometric analysis) method using a 2-thiobarbituric acid-reactive substance (TBARS). The results are shown in FIG. 5.

Figure 6:
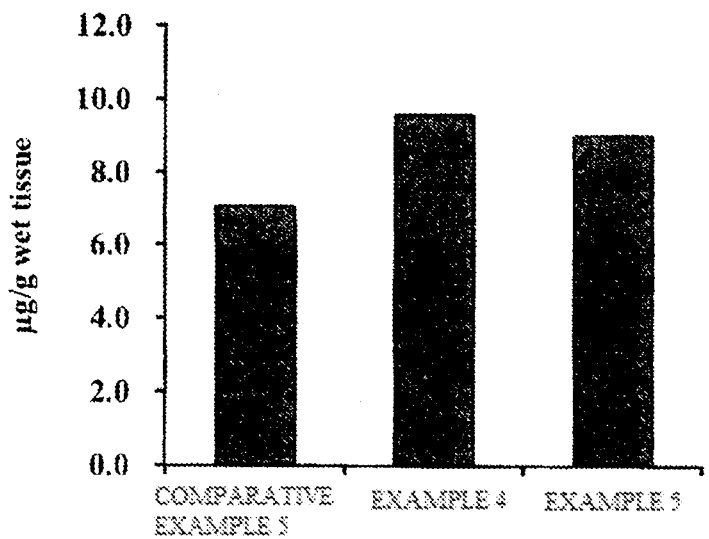
FIG. 6 Example; this is a drawing comparing an α-tocopherol content at pectoralis major muscle.

<Determination of α-tocopherol content in pectoralis major muscle> A pectoralis major muscle tissue at 28 days-old was collected, and an α-tocopherol content was determined by the HPLC method. The results are shown in FIG. 6.

Figure 7:
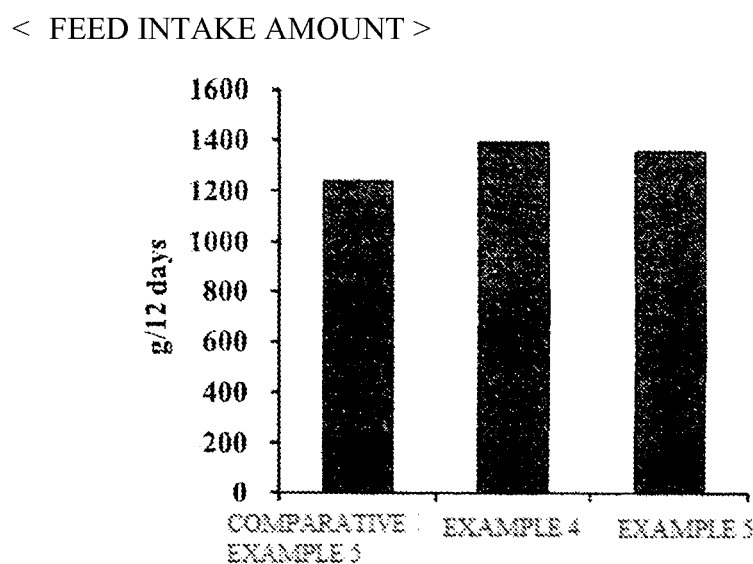
FIG. 7 Example; this is a drawing comparing a feed intake amount.

<Comparison of feed intake amount> A feed intake amount from the 16 days-old to the 28 days-old was measured every two days, and the total feed intake amounts for 12 days were compared. The results are shown in FIG. 7.

Example 5

In Example 4, a feed was prepared in the same manner as in Example 4 except for changing the amount of the additive for a feed to be added to the formulating material for the feed to 5.00% by weight (2.70% by weight with a dry basis), and fed, and observation of shape of small intestine, determination of a peroxide in the pectoralis major muscle, determination of an α-tocopherol content in the pectoralis major muscle, and measurement of a feed intake amount were carried out.

The composition, metabolic energy, gross energy and crude protein of the feed were shown in Table 2.

The height of villus is shown in FIG. 2, the depth of crypt is shown in FIG. 3, and the ratio of the height of villus to the depth of crypt is shown in FIG. 4, respectively.

Also, a lipid peroxide amount in the pectoralis major muscle is shown in FIG. 5, and an α-tocopherol content in the pectoralis major muscle is shown in FIG. 6, respectively.

Furthermore, the total feed intake amounts for 12 days from 16 to 28 days-old are shown in FIG. 7.

Comparative Example 5

In Examples 4 and 5, a feed was prepared in the same manner as in Example 4 except for not adding the additive for a feed to the formulating material for the feed, and fed, and observation of shape of small intestine, determination of a peroxide in the pectoralis major muscle, determination of an α-tocopherol content in the pectoralis major muscle, and measurement of a feed intake amount were carried out.

The composition, metabolic energy, gross energy and crude protein of the feed were shown in Table 2.

The height of villus is shown in FIG. 2, the depth of crypt is shown in FIG. 3, and the ratio of the height of villus to the depth of crypt is shown in FIG. 4, respectively.

Also, a lipid peroxide amount in the pectoralis major muscle is shown in FIG. 5, and an α-tocopherol content in the pectoralis major muscle is shown in FIG. 6, respectively.

Furthermore, the total feed intake amounts for 12 days from 16 to 28 days-old are shown in FIG. 7.

TABLE 2

<Feed composition>

| | Comp. Example 5 | Example 4 | Example 5 |
|---|---|---|---|
| Additive for feed | 0.00 | 1.00 | 5.00 |
| (Dry basis calculated amount | 0.00 | 0.54 | 2.70) |
| Formulating material for feed | | | |
| Corn | 53.45 | 52.45 | 47.89 |
| Soybean oil | 37.35 | 37.35 | 37.55 |
| Corn oil | 5.00 | 5.00 | 5.35 |
| Calcium hydrogen phosphate (dihydrate) | 1.75 | 1.75 | 1.75 |
| Calcium carbonate | 1.03 | 1.03 | 1.03 |
| Sodium chloride | 0.33 | 0.33 | 0.33 |
| Magnesium sulfate | 0.30 | 0.30 | 0.30 |
| DL-methionine | 0.25 | 0.25 | 0.26 |
| Lysine hydrochloride | 0.04 | 0.04 | 0.04 |
| Glucose | 0.17 | 0.17 | 0.17 |
| Choline chloride | 0.13 | 0.13 | 0.13 |
| Vitamin Core | 0.10 | 0.10 | 0.10 |
| Mineral Core | 0.10 | 0.10 | 0.10 |
| Total | 100.00 | 100.00 | 100.00 |
| | (The above units are all % by weight) | | |
| Metabolic energy (Mcal/kg) | 3.12 | 3.11 | 3.08 |
| Gross energy (Mcal/kg) | 4.15 | 4.13 | 4.09 |
| Crude protein (% by weight) | 21.05 | 21.03 | 21.00 |

(Among the above-mentioned units, those shown by % by weight, and otherwise specifically mentioned are all wet basis)

<Evaluation of feeding test> It has been known that the shape of small intestine is potently reflected by the effect of stress, in particular, when the stress is applied, the height of villus becomes low and crypt becomes deep. It has also been known that metabolism becomes good when the ratio of the height of villus to the depth of crypt is high.

From the results shown in FIGS. 2 to 4, in Examples 4 and 5, it can be understood that the state that the ratio of the height of villus to the depth of crypt is high as compared with that of Comparative example 5, so that these samples are excellent in metabolism. According to these results, it can be understood that growth performance is improved and an effect to gain a weight can be obtained.

In addition, from the results shown in FIG. 5, in Examples 4 and 5, lipid peroxide is suppressed as compared with that of Comparative example 5, so that it can be understood that the meat quality of broiler chickens can be improved.

Moreover, from the results shown in FIG. 6, in Examples 4 and 5, consumption of the α-tocopherol in the pectoralis major muscle is suppressed according to an antioxidative effect by the polyphenol, etc., and the remained amount of the α-tocopherol in the pectoralis major muscle is much as compared with that of Comparative example 5, so that it can be understood that the meat quality of broiler chickens can be improved.

Furthermore, from the results shown in FIG. 7, in Examples 4 and 5, a feed intake amount is increased in the feed to which the additive for a feed obtained in Example 1 has been mixed as compared with that of Comparative example 5, so that it can be understood that palatability of the feed is improved.

The invention claimed is:

1. A method for preparing a feed which comprises: a step for extracting a polyphenol, α-tocopherol and xyloses from EFB, and preparing an additive for a feed that includes the extracted polyphenol, α-tocopherol and xyloses; and a step for adding the additive for a feed to a formulating material for a feed.

\* \* \* \* \*